(12) United States Patent
Nishtala

(10) Patent No.: US 8,146,210 B2
(45) Date of Patent: Apr. 3, 2012

(54) SUPPORT CLAMP FOR MEDICAL LINE

(75) Inventor: Vasu Nishtala, Snellville, GA (US)

(73) Assignee: C.R. Bard, Inc., Covington, GA (US)

( * ) Notice: Subject to any disclaimer, the term of this patent is extended or adjusted under 35 U.S.C. 154(b) by 821 days.

(21) Appl. No.: 12/175,247

(22) Filed: Jul. 17, 2008

(65) Prior Publication Data
US 2009/0139061 A1 Jun. 4, 2009

Related U.S. Application Data (60) Provisional application No. 60/950,203, filed on Jul. 17, 2007.

(51) Int. Cl.
F16L 3/10 (2006.01)
(52) U.S. Cl. .......................... 24/16 R; 24/518
(58) Field of Classification Search .......... 24/16 R, 24/16 PB, 17 A, 17 AP, 484, 518; 248/74.1–74.3, 248/68.1, 69; 604/174, 177–180
See application file for complete search history.

(56) References Cited

U.S. PATENT DOCUMENTS

| | | |
|---|---|---|
| 2,525,398 A | 10/1950 | Collins |
| 2,707,953 A | 5/1955 | Ryan |
| 3,046,984 A | 12/1958 | Eby |
| 2,893,671 A | 7/1959 | Flora et al. |
| 3,059,645 A | 10/1962 | Hasbrouck et al. |
| 3,064,648 A | 11/1962 | Bujan |
| 3,482,569 A | 12/1969 | Raffaelli, Sr. |
| 3,556,096 A | 1/1971 | Fuller et al. |
| 3,630,195 A | 12/1971 | Santomieri |
| 3,677,250 A | 7/1972 | Thomas |
| 3,766,915 A | 10/1973 | Rychlik |
| 3,856,020 A | 12/1974 | Kovac |
| 3,896,527 A | 7/1975 | Miller et al. |
| 3,906,946 A | 9/1975 | Nordstrom |
| 3,973,565 A | 8/1976 | Steer |
| 3,993,081 A | 11/1976 | Cussell |
| 4,020,835 A | 5/1977 | Nordstrom et al. |
| 4,057,066 A | 11/1977 | Taylor |
| 4,059,105 A | 11/1977 | Cutruzzula et al. |
| 4,129,128 A | 12/1978 | McFarlane |
| 4,133,307 A | 1/1979 | Ness |
| 4,142,527 A | 3/1979 | Garcia |
| 4,149,539 A | 4/1979 | Cianci |
| 4,161,177 A | 7/1979 | Fuchs |
| 4,170,995 A | 10/1979 | Levine et al. |

(Continued)

FOREIGN PATENT DOCUMENTS
CA 2 228 747 2/1997
(Continued)

Primary Examiner — James Brittain
(74) Attorney, Agent, or Firm — Knobbe Martens Olson & Bear, LLP (57) ABSTRACT

A support device or clamp connects to a soft, flexible tube, such as a medical line, to hold the tube in an open condition. The device includes a flexible body with interengaging structure that biases the body into a desired shape when in a closed position or condition. The desired shape generally matches the outer shape of the medical line. An adhesive is disposed on the support device so as to contact the secured portion of the medical line to inhibit the walls of the line from collapsing or creasing. The support device may include base structure that has an adhesive lower surface for attaching the support device to a patient's skin.

18 Claims, 5 Drawing Sheets

U.S. PATENT DOCUMENTS

| | | | |
|---|---|---|---|
| 4,193,174 | A | 3/1980 | Stephens |
| 4,224,937 | A | 9/1980 | Gordon |
| 4,248,229 | A | 2/1981 | Miller |
| 4,250,880 | A | 2/1981 | Gordon |
| 4,316,461 | A | 2/1982 | Marais et al. |
| 4,326,519 | A | 4/1982 | D'Alo et al. |
| 4,333,468 | A | 6/1982 | Geist |
| 4,362,156 | A | 12/1982 | Feller, Jr. et al. |
| 4,392,853 | A | 7/1983 | Muto |
| 4,392,857 | A | 7/1983 | Beran |
| 4,397,647 | A | 8/1983 | Gordon |
| 4,449,975 | A | 5/1984 | Perry |
| 4,453,933 | A | 6/1984 | Speaker |
| 4,480,639 | A | 11/1984 | Peterson et al. |
| 4,490,141 | A | 12/1984 | Lacko et al. |
| 4,502,477 | A | 3/1985 | Lewis |
| 4,516,293 | A | 5/1985 | Beran |
| 4,517,971 | A | 5/1985 | Sorbonne |
| 4,534,762 | A | 8/1985 | Heyer |
| 4,569,348 | A * | 2/1986 | Hasslinger .................. 604/179 |
| 4,579,120 | A | 4/1986 | MacGregor |
| 4,583,976 | A | 4/1986 | Ferguson |
| 4,633,863 | A | 1/1987 | Filips et al. |
| 4,650,473 | A | 3/1987 | Bartholomew et al. |
| 4,659,329 | A | 4/1987 | Annis |
| 4,699,616 | A | 10/1987 | Nowak et al. |
| 4,708,512 | A * | 11/1987 | Allert ........................ 403/344 |
| 4,711,636 | A | 12/1987 | Bierman |
| 4,726,716 | A | 2/1988 | McGuire |
| 4,742,824 | A | 5/1988 | Payton et al. |
| 4,808,162 | A | 2/1989 | Oliver |
| 4,823,789 | A | 4/1989 | Beisang, III |
| 4,838,878 | A | 6/1989 | Kalt et al. |
| 4,852,844 | A | 8/1989 | Villaveces |
| 4,857,058 | A | 8/1989 | Payton |
| 4,863,432 | A | 9/1989 | Kvalo |
| 4,897,082 | A | 1/1990 | Erskine |
| 4,898,587 | A | 2/1990 | Mera |
| 4,919,654 | A | 4/1990 | Kalt |
| 4,950,285 | A | 8/1990 | Wilk |
| 4,955,864 | A | 9/1990 | Hajduch |
| 4,976,700 | A | 12/1990 | Tollini |
| 5,000,741 | A | 3/1991 | Kalt |
| 5,037,397 | A | 8/1991 | Kalt et al. |
| 5,073,170 | A | 12/1991 | Schneider |
| 5,079,804 | A | 1/1992 | Gregurich et al. |
| 5,084,026 | A | 1/1992 | Shapiro |
| 5,098,399 | A | 3/1992 | Tollini |
| 5,100,393 | A | 3/1992 | Johnson |
| 5,123,913 | A | 6/1992 | Wilk et al. |
| 5,147,322 | A | 9/1992 | Bowen et al. |
| 5,156,641 | A | 10/1992 | White |
| 5,188,609 | A | 2/1993 | Bayless et al. |
| 5,192,273 | A | 3/1993 | Bierman et al. |
| 5,192,274 | A | 3/1993 | Bierman |
| 5,195,981 | A | 3/1993 | Johnson |
| 5,224,935 | A | 7/1993 | Hollands |
| 5,226,892 | A | 7/1993 | Boswell |
| 5,234,185 | A | 8/1993 | Hoffman et al. |
| 5,266,401 | A | 11/1993 | Tollini |
| 5,292,312 | A | 3/1994 | Delk et al. |
| 5,304,146 | A | 4/1994 | Johnson et al. |
| 5,306,243 | A | 4/1994 | Bonaldo |
| 5,314,411 | A | 5/1994 | Bierman |
| 5,334,186 | A | 8/1994 | Alexander |
| 5,338,308 | A | 8/1994 | Wilk |
| 5,342,317 | A | 8/1994 | Claywell |
| 5,344,406 | A | 9/1994 | Spooner |
| 5,346,479 | A | 9/1994 | Schneider |
| 5,354,282 | A | 10/1994 | Bierman |
| 5,368,575 | A | 11/1994 | Chang |
| 5,380,293 | A | 1/1995 | Grant |
| 5,389,082 | A | 2/1995 | Baugues et al. |
| 5,398,679 | A | 3/1995 | Freed |
| 5,403,285 | A | 4/1995 | Roberts |
| 5,413,562 | A | 5/1995 | Swauger |
| 5,443,460 | A | 8/1995 | Miklusek |
| 5,456,671 | A | 10/1995 | Bierman |
| 5,468,231 | A | 11/1995 | Newman et al. |
| 5,470,321 | A | 11/1995 | Forster et al. |
| D364,922 | S | 12/1995 | Bierman |
| 5,147,322 | A | 1/1996 | Bowen et al. |
| 5,496,282 | A | 3/1996 | Militzer et al. |
| 5,496,283 | A | 3/1996 | Alexander |
| 5,499,976 | A | 3/1996 | Dalton |
| 5,520,656 | A | 5/1996 | Byrd |
| 5,527,293 | A | 6/1996 | Zamierowski |
| D375,355 | S | 11/1996 | Bierman |
| 5,626,565 | A | 5/1997 | Landis et al. |
| 5,632,274 | A | 5/1997 | Quedens et al. |
| 5,637,098 | A | 6/1997 | Bierman |
| 5,672,159 | A | 9/1997 | Warrick |
| 5,676,137 | A | 10/1997 | Byrd |
| 5,681,290 | A | 10/1997 | Alexander |
| 5,685,859 | A | 11/1997 | Kornerup |
| 5,690,617 | A | 11/1997 | Wright |
| 5,693,032 | A | 12/1997 | Bierman |
| 5,722,959 | A | 3/1998 | Bierman |
| 5,855,591 | A | 1/1999 | Bierman et al. |
| 5,944,696 | A | 8/1999 | Bayless et al. |
| 6,074,368 | A | 6/2000 | Wright |
| 6,113,577 | A | 9/2000 | Hakky et al. |
| 6,132,398 | A | 10/2000 | Bierman et al. |
| 6,283,945 | B1 | 9/2001 | Bierman |
| 6,361,523 | B1 | 3/2002 | Bierman |
| 6,413,240 | B1 | 7/2002 | Bierman et al. |
| 6,419,660 | B1 | 7/2002 | Russo |
| 6,428,514 | B1 | 8/2002 | Goebel et al. |
| 6,458,104 | B2 | 10/2002 | Gautsche |
| 6,500,154 | B1 | 12/2002 | Hakky et al. |
| 6,663,600 | B2 | 12/2003 | Bierman et al. |
| 6,951,550 | B2 | 10/2005 | Bierman |
| 7,018,362 | B2 | 3/2006 | Bierman et al. |
| 2005/0137496 | A1 | 6/2005 | Walsh et al. |
| 2005/0192539 | A1 | 9/2005 | Bierman et al. |
| 2006/0129103 | A1 | 6/2006 | Bierman et al. |
| 2006/0233652 | A1 | 10/2006 | Kim et al. |
| 2007/0035123 | A1 * | 2/2007 | Holt et al. ................ 285/23 |
| 2007/0142782 | A2 | 6/2007 | Bierman |
| 2007/0142784 | A1 | 6/2007 | Dikeman et al. |
| 2007/0265572 | A1 | 11/2007 | Smith et al. |
| 2007/0276335 | A1 | 11/2007 | Bierman |
| 2008/0097334 | A1 | 4/2008 | Dikeman et al. |
| 2009/0139061 | A1 | 6/2009 | Nishtala |

FOREIGN PATENT DOCUMENTS

| | | |
|---|---|---|
| CA | 2 208 577 | 5/1997 |
| CA | 2 310 030 | 5/1999 |
| CA | 2 402 507 | 9/2001 |
| CA | 2 483 995 | 4/2004 |
| DE | 31 10 023 A1 | 9/1982 |
| DE | 88 11 131 8 U | 9/1988 |
| EP | 0064 284 A2 | 4/1982 |
| EP | 0274 418 A2 | 5/1988 |
| EP | 0356 683 A | 7/1990 |
| EP | 0470 709 A1 | 12/1992 |
| EP | 0 931 560 | 7/1999 |
| FR | 2381529 | 2/1978 |
| GB | 2219034 | 11/1989 |
| GB | 2288542 A | 10/1995 |
| JP | S60-051377 | 4/1985 |
| JP | H04-037448 | 3/1992 |
| JP | H08-257138 | 8/1996 |
| NL | 1 015 663 | 1/2002 |
| WO | WO 80/01458 | 7/1980 |
| WO | WO 92/19309 | 11/1992 |
| WO | WO 96/26756 | 9/1996 |
| WO | WO 2007/028007 | 3/2007 |
| WO | WO 2008/116119 | 9/2008 |

* cited by examiner

SUPPORT CLAMP FOR MEDICAL LINE

CROSS-REFERENCE TO RELATED APPLICATION

This application claims the benefit of U.S. Provisional Application No. 60/950,203, filed on Jul. 17, 2007, which is incorporated herein by reference in its entirety.

BACKGROUND OF THE INVENTION

1. Field of the Invention

This invention relates to support devices used with medical lines attached to a patient. In particular, this invention relates to support or securement devices used with soft, flexible tubes or drains.

2. Description of the Related Art

Certain medical lines attached to patients are relatively soft and flexible. Typically, larger, flexible tubes are used as drains, such as rectal drains or external ventricular drains. Larger, flexible tubes are also used as big bore chest tubes, for example, where a larger volume of fluid needs to be transported. A problem experienced with these soft flexible tubes is the possibility of collapse of the line or potential for kinking or bending of the line thereby creating an obstruction. An associated problem is how to secure such a line to the patient to ensure that the line does not move or become disconnected from the patient.

A common practice is to merely tape the line to the patient's skin. However, a taped line may shift. More importantly, taping a soft line to a patient's skin can compress the line and obstruct or occlude fluid flow.

There is a need for a support device that can connect to a soft flexible tube and ensure free fluid flow within the tube. There is also a need for a support device that can be reliably used by medical personnel.

SUMMARY

One aspect of the invention is directed to a support clamp for use with a flexible hollow line. The clamp includes an elongated body that has two ends and an inner surface. The body is movable between an open position in which at least a portion of the line can be received by the clamp and a closed position in which the body defines a passageway configured to surround at least a received portion of the line. The clamp further includes an adhesive disposed on at least a portion of the inner surface of the passageway and configured to contact at least a portion of the received line. The clamp further includes interengaging structure configured to releasably secure the two ends in the closed position and bias at least a portion of the body in a generally outwardly direction to form a shape that generally matches the shape of the secured portion of the line.

Another aspect is directed to a support clamp for use with a medical line that has a passage therethrough. The clamp includes a flexible body that has opposed ends and adhesive disposed on at least a portion of a surface of the flexible body. The clamp further includes interengaging structure disposed on the opposed ends of the flexible body to selectively join the ends of the body and form the flexible body into a generally ring-like shape with the adhesive facing inwardly to form an adhesive lined conduit. The adhesive is configured to contact a medical line so as to maintain a passage in the medical line in an open condition.

Another aspect is directed to a method of supporting a flexible hollow line. The method includes providing a flexible hollow line with a passage therein, providing a clamp formed of a flexible body with a tacky surface, and positioning the clamp around the hollow line. The method further includes closing the clamp around the hollow line so that the tacky surface adheres to at least two opposite sides of the hollow line and the flexible body of the clamp is biased outwardly into a generally rounded shape pulling the sides of the hollow line apart to inhibit occlusion of the passage within the hollow line.

Another aspect is directed to a support clamp that includes a body having interengaging structure. At least a portion of the body is movable between an unrestrained shape in which the interengaging structure is disengaged, and a restrained shape in which the interengaging structure is engaged. An adhesive is configured to contact the medical line at least when the medical line is secured within the clamp and the body is in the restrained shape.

Another aspect of the invention is directed to a support clamp for use with a flexible hollow line. The clamp includes an elongated body having two opposed ends, a first surface, and a second surface. The clamp further includes a closure disposed on each of the opposed ends, such that the opposed ends can be selectively coupled together to form the body into a generally rounded conduit with the first surface facing inwardly and the second surface facing outwardly. The clamp further includes an adhesive disposed on the first surface of the body so that the conduit has an interior tacky surface. The body may be formed of flexible material so that when the closure is coupled the body is biased outwardly forming the generally rounded conduit.

Another aspect is directed to a support clamp for use with a medical line that has a passage therethrough. The clamp includes a flexible body having opposed ends, adhesive disposed on a surface of the flexible body, and a closure disposed on the opposed ends of the flexible body to selectively join the ends of the body and form the flexible body into a generally ring-like shape with the adhesive facing inwardly to form an adhesive lined conduit that is configured to surround and engage a medical line so as to maintain a passage in the medical line in an open condition.

Another aspect is directed to a method of supporting a flexible hollow line. The method includes providing a flexible hollow line with a passage therein and providing a clamp formed of a flexible body with a tacky surface. The method further includes positioning the clamp around the hollow line, and closing the clamp around the hollow line so that the tacky surface adheres to at least two opposite sides of the hollow line and the flexible body of the clamp is biased outwardly into a generally rounded shape to pull the sides of the hollow line apart and maintain an open passage within the hollow line.

In certain embodiments, the device safely clamps to a flexible hollow line and maintains it in an open condition. The device is preferably easy to install and manipulate.

These and other aspects of the present invention will become readily apparent to those skilled in the art from the following detailed description of the preferred embodiments, which refers to the attached figures. The invention is not limited, however, to the particular embodiments that are disclosed.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

DETAILED DESCRIPTION OF THE PREFERRED EMBODIMENTS

The present embodiments relate to a support device for use with a soft flexible line, such as a tube or drain used with a medical patient. In general, the support clamp 10 is usable with catheters, fluid supply, and drainage lines. The lines include, without limitation, various medical articles such as rectal drains, external ventricular drains, chest tubes, feeding tubes, surgical drainage tubes, nasogastric tubes, central venous catheters, peripherally inserted central catheters, Foley catheters, and hemodialysis catheters. Moreover, the support device is not limited to medical lines and could be used with any type of flexible tube in which it is desired to maintain a passage therein and inhibit collapse of the tubing. One skilled in the art may also find additional applications for the devices and systems disclosed herein. Thus, the illustrations and descriptions of the support device in connection with the medical lines are merely exemplary of some possible applications of the support device.

Figure 2:
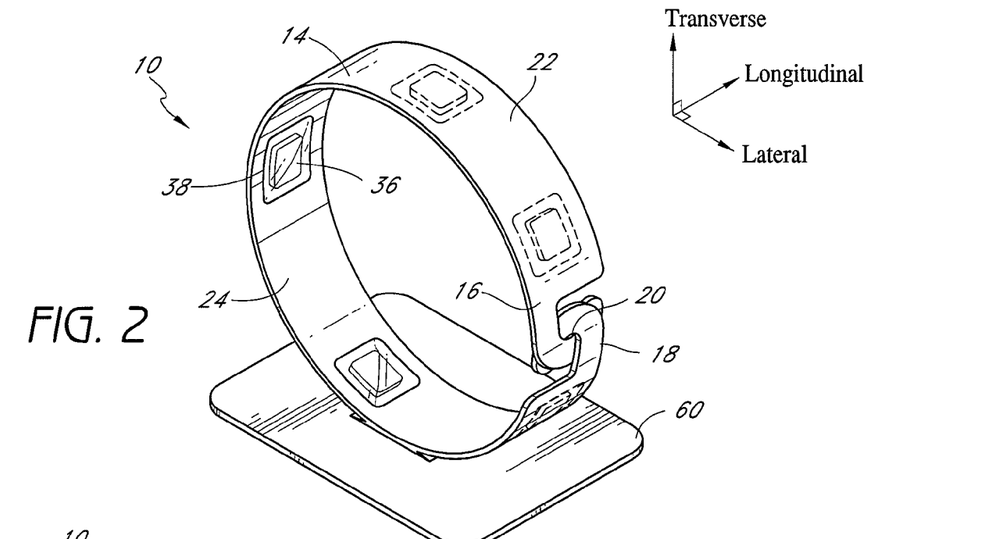
FIG. 2 is a perspective view of a support clamp from FIG. 1 in a closed position.

To assist in the description of these components of the support device, the following coordinate terms are used. A "longitudinal axis" is generally parallel to the major axis of the medical line (further described below). A "lateral axis" is normal to the longitudinal axis and is generally parallel to the plane of a base 60, as seen in FIG. 2. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "upper," "lower," "top," "bottom," and the like, which also are used to describe the present support device, are used in reference to the illustrated orientation of the embodiment. A detailed description of a preferred embodiment of the support device, and its associated method of use, now follows.

The support device system described herein is especially adapted to arrest axial movement of the medical line 12, as well as hold the medical line against the patient. For this purpose, the support clamp assembly 10 can utilize one or more retention mechanisms. The support clamp assembly 10 accomplishes this though without meaningfully impairing (i.e., substantially occluding) the fluid flow through the medical line 12 to a degree that would create complications. As described below, such retention mechanisms involve, among others, retaining structure either aligned with or positioned within the passageway, a securement barb(s) and/or friction ridge(s) that bites into the medical line without substantially occluding the medical line.

The support clamp assembly 10 also desirably releasably engages the medical line 12. This allows the medical line 12 to be disconnected from the support clamp assembly 10, and from the patient, for any of a variety of known purposes. For instance, the healthcare provider can want to remove the medical line from the support clamp assembly 10 to ease disconnection of a catheter from the medical line or to clean the patient. The disengagement of the medical line from the support clamp assembly 10, however, can be accomplished without removing the support clamp assembly 10 from the patient.

Figure 1:
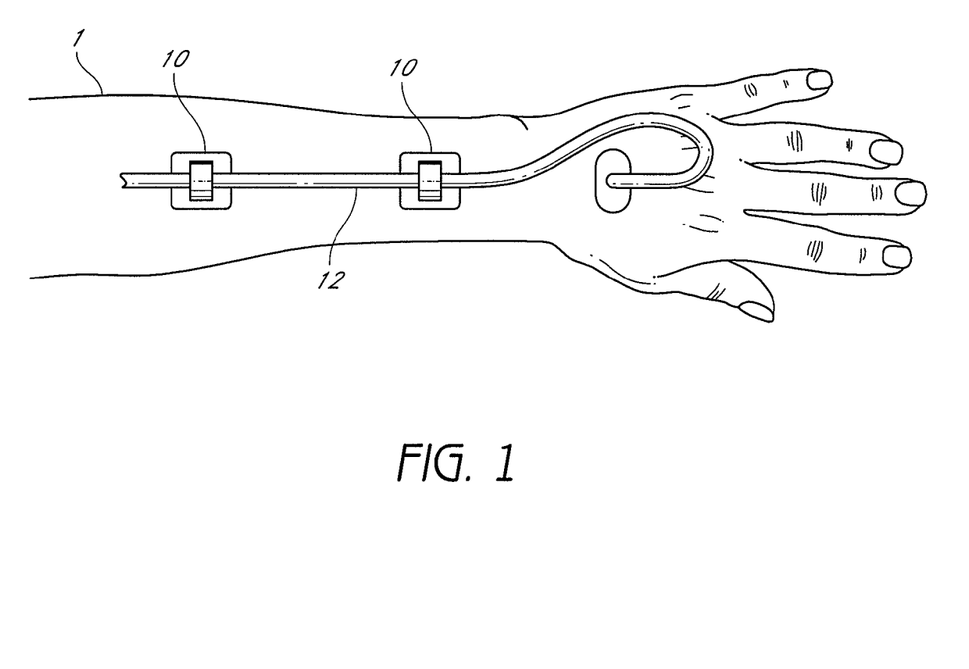
FIG. 1 is a plan view of a plurality of support clamps securing a medical tube to a patient in accordance with a preferred embodiment of the present invention.

FIG. 1 is a diagram of a medical line 12 attached to a patient 1 using a plurality of support clamps 10. As shown in FIG. 1, the tube 12 may be part of a peripheral intravenous line. The support clamps 10 provide the dual functionality of securing the tube 12 to the patient 1, and inhibiting the collapse of the tube 12 by providing additional circumferential support.

FIG. 2 is a perspective view of a support clamp in the closed position according to an embodiment of the invention. The support clamp assembly 10 includes an elongated body 14 that has two ends 16 and 18. The body 14 can be any width depending on the desired use, including a thin strip or wide band. The body 14 comprises an outer surface 22 and an inner surface 24. Disposed upon the inner surface is an adhesive 36, which may be covered by a release sheet 38. The ends 16, 18 include interengaging structure 20, as explained below.

The body 14 of the support clamp may be made of a flexible, resilient material, such as plastic. Other suitable flexible materials include, for example, but without limitation, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. The material has a memory or preference for a desired shape of an internal passageway formed through the body 14. Preferably, the desired shape generally matches an outer circumference of the medical line to be secured by the clamp 10. The body 14 may be formed of a medically compatible material, such as a non-allergenic polymer. When flexed to a closed position or condition, the body 14 will arch and tend to return to its original or desired shape. Of course, any sheet material that is flexible and resilient could be used to form the body 14, including stainless steel or paper.

To firmly hold the secured portion of the medical line within the passageway, the support clamp 10 includes interengaging structure. The interengaging structure may be located at the ends 16, 18 of the support clamp 10. The interengaging structure releasably couples the ends in the closed position. In this way, the ends 16, 18 of the body 14 form the interengaging structure when in the closed position or condition. In the embodiment illustrated in FIG. 2, hooks on each end of the support clamp 10 secure the support clamp 10 in the closed position. Of course other interengaging structure 10 can form the interengaging structure. For example, a latch mechanism, hook and loop fastener, or other securement structure known in the art. The interengaging structure may be a separate structure from the clamp 10. For example, an interengaging structure in the form of a strap could wrap around and hold the clamp 10 in the closed position.

When the interengaging structure or ends 16, 18 are secured, the body 14 is preferably biased and bends or flexes into the desired shape. For example, the desired shape could be a generally ring-like shape which generally matches the outside circumference of a medical line 12 that has a tubular shape. Because the body 14 is made of sheet material that can flex, it becomes generally rounded when the ends 16, 18 are secured and forms the passageway for the medical line 12. To support tubular medical lines 12, the shape of the passageway is preferably generally rounded or ring-like meaning it can be circular or non-circular, such as an egg-shape, oval, or lidded cup. The passageway through the clamp 10 receives the medical line 12.

Disposed upon at least a portion of the inner surface 24 of the body 14 is an adhesive 36. The adhesive 36 may cover the entire inner surface 24 or multiple portions of the inner surface 24. In the illustrated embodiment of FIG. 2, the adhesive 36 is non-contiguously disposed in a plurality of locations. In other embodiments, the adhesive 36 may substantially cover the entire inner surface 24. In the illustrated embodiment of FIG. 2, the adhesive 36 is disposed in a plurality of square-like regions. In other embodiments, the adhesive 36 may be disposed in one or more regions, each region having the shape of a square, a spot, a strip, a dot, a sheet, or any other shape.

The adhesive 36 may be covered by one or more release sheet(s) 38. In the illustrated embodiment of FIG. 2, a plurality of release sheets are disposed on top of the adhesive regions on the inner surface 24. In other embodiments, a single release sheet 38 may be disposed on one or more adhesive regions or on a single contiguous adhesive layer 36 disposed on the inner surface 24.

The clamp 10 may further include a base 60. The base 60 can be configured in a wide variety of shapes, such as circular, square, triangular or the like in order to suit a particular application. The longitudinal dimension of the base 60 though desirably is sufficiently long to provide stability to the medical line 12 along its length.

The base 60 provides a mounting surface for attaching the clamp 10 to a patient's skin. For example, the clamp 10 may be mounted on the base 60 as is illustrated in FIG. 2. The base 60 can be affixed to the body 14 by stitching, adhesive, heat seal, or any other suitable fastener. The base 60 can be secured to a patient's skin, by adhesive or a strap, for example, to serve as a fixed mount for the medical line passing through the clamp 10.

The base 60 may be provided with an adhesive bottom surface for securing the clamp 10 directly to the patient or indirectly to the patient via, for example, an anchor pad. For the later embodiment, the adhesive adheres the base 60 to the anchor pad which itself is adhered to the patient.

The adhesive bottom surface can be formed of any adhesive that is biocompatible and can be applied with known methods, including transfer tape and sputtering. The adhesive may be a medical-grade adhesive layer that can be either diaphoretic or nondiaphoretic, depending on the particular application. A release sheet can be disposed over the adhesive bottom surface for removal upon application to a patient's skin. In one embodiment, the release sheet resists tearing and is divided into a plurality of pieces to assist in attachment to a patient. The sheet can be split along its center line so that only half of the adhesive surface is exposed at a time. It can extend beyond at least one edge of the base 60 to facilitate removal of the sheet from the adhesive surface. Any known material can be used as the sheet. For example, one suitable material is polycoated, siliconized paper. In other embodiments, multiple support clamps 10 are attached via the adhesive bottom surface to a single release sheet. The release sheet may be perforated such that individual clamps may be easily obtained without removing the release sheet from the adhesive bottom surface.

Figure 3:
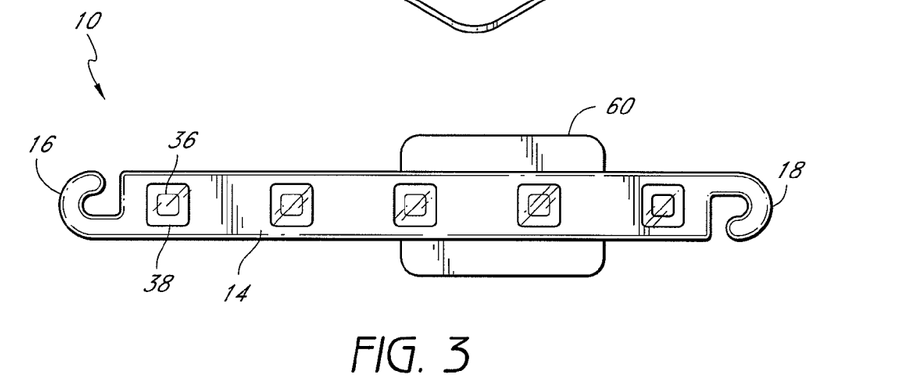
FIG. 3 is a plan view of the support clamp from FIG. 2 in an open position.

According to certain embodiments, the inner surface of the passageway can have an adhesive 36 to adhere the clamp to the medical line 12. FIG. 3 is a top view of a support clamp in the open position, in which the adhesive 36 is covered by a removable release liner 38. The adhesive 36 can be formed as a solid layer or as spots of adhesive, as seen in FIG. 3. Any adhesive configuration would be suitable including strips, dots, patches or sheets. The adhesive 36 forms a tacky surface on the interior of the passageway to adhere to a line 12 disposed in the clamp 10. By adhering to the exterior surface of the medical line 12 within the clamp 10, the walls of the line 12 will be held in an open position to allow the free flow of fluid within the line 12. Accordingly, while the adhesive 36 covers the entire inner surface in some embodiments, in other embodiments, the inner surface is only provided with adhesive 36 on opposing spots to hold the tubular walls apart. Any suitable adhesive can be used, such as a pressure sensitive adhesive.

The adhesive 36 may be added during manufacture of the clamp 10 or attached during use, for example, by means of double stick tape. If provided during manufacture, a release sheet 38 may be mounted over the adhesive surface 36 to prevent inadvertently exposing the tacky surface prior to placement of the line. The adhesive may have a small amount of tack so that it will adhere to a medical line, but not permanently stick to other surfaces. Any suitable material can be used for the release sheet 38, as is known, such as silicone coated polyester film. Other suitable materials include films such as high density polyethylene, polypropylene, polyolefin, or siliconcoated paper.

The interengaging structure 20 between the ends of the support clamp 10 can take various forms. Preferably, the interengaging structure 20 forms a secure interlock that is simple to manipulate. As one of the uses for the support clamp 10 is for patient care, it is advantageous that a caregiver be able to easily and quickly secure the clamp 10 to a medical line on a patient, even with one hand if necessary. One type of interengaging structure 20 that is easy to manipulate is a pair of complementary interlocking hooks, as seen in FIG. 2. Of course, other suitable types of interengaging structures can be used, including snap-fit, ball and socket, adhesive, Velcro®, twist ties or buckles, for example. Any of these types of interengaging structures may be adjustable.

Figure 4:
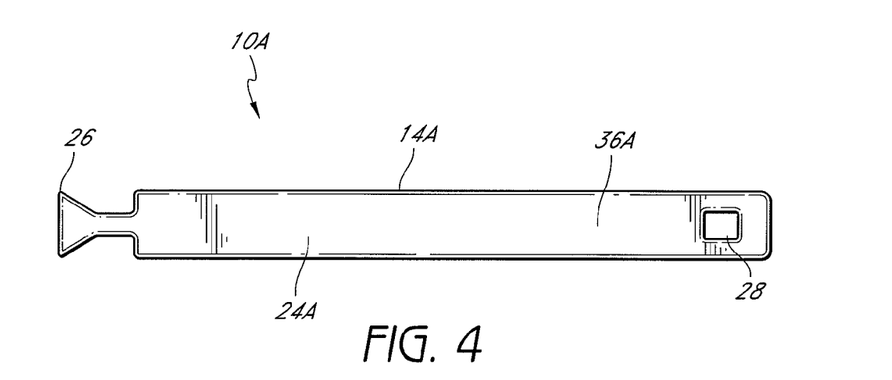
FIG. 4 is a plan view of another embodiment of a support clamp in an open position.

FIG. 4 shows an alternate embodiment of a support clamp 10A. The support clamp 10A comprises a body 14A having an inner surface 24A entirely covered with adhesive 36A. Unlike the support clamp described with reference FIG. 2, the embodiment illustrated in FIG. 4 does not have a base. Of course the embodiment illustrated in FIG. 4 could include a base. The support clamp 10A illustrated in FIG. 4 also differs from previously shown embodiments in that interengaging structure is comprised of a hook 26 and slot 28. The hook 26 is disposed at one end 16A of the body 14A and the slot 28 is disposed at the opposite end 18B of the body 14A. The hook 26 is configured to engage with the slot 28.

Figure 5A:
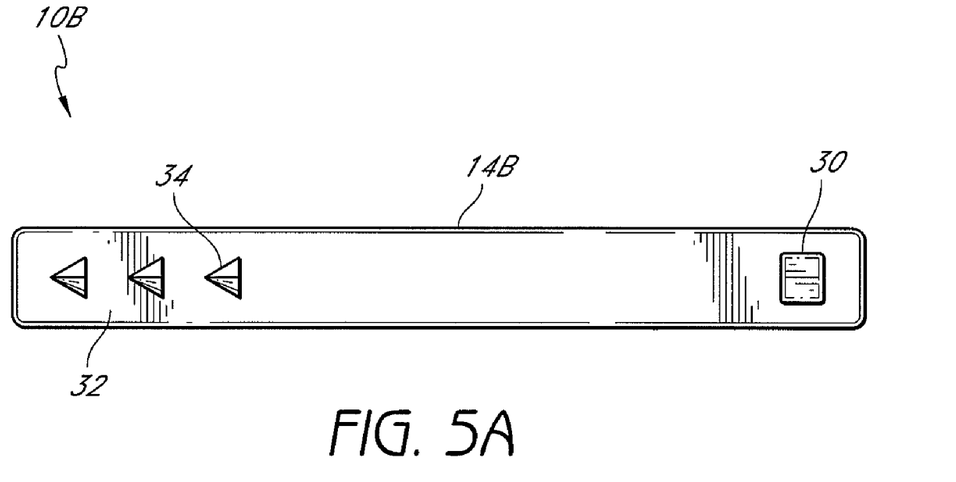
FIG. 5A is a plan view of another embodiment of a support clamp in an open position.
Figure 5B:
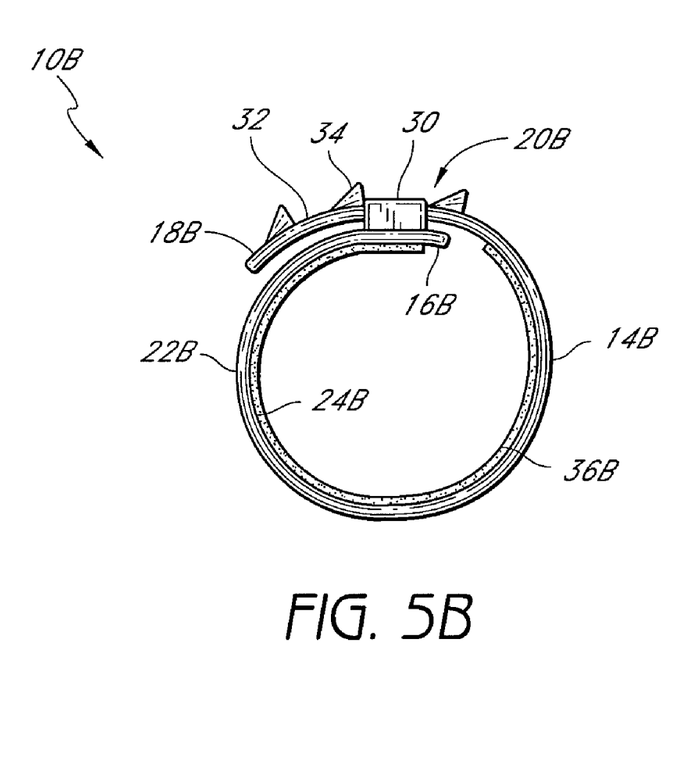
FIG. 5B is a side view of the support clamp of FIG. 5A in a closed position.

FIGS. 5A and 5B show yet another embodiment of a support clamp 10B. The support clamp 10B, like the embodiment shown in FIG. 4, comprises a body 14B with an adhesive 36B disposed upon the inner surface 24B. The support clamp 10B differs from previously described embodiments in that the interengaging structure is composed of a receptacle 30 and a projection 32. The projection 32 is in the form of one or more teeth 34 protruding from the body 14B.

The embodiment illustrated in FIGS. 5A and 5B further allows the caregiver to adjust the circumference of the support clamp 10B to match the size of the particular line to which it will be secured. Another potential advantage of the embodiment illustrated in FIGS. 5A and 5B relates to the adhesive 36B disposed upon the inner surface 24B of the body 14B. As the clamp 10B is placed around a medical line, tightening the clamp 10B causes the pressure sensitive adhesive 36B to adhere to the medical line. The clamp loosens slightly until the hook 34 contacts the receptacle 30. As the inner surface 24B of the body 14B is adhered to the line by the adhesive 36B, this acts to stretch the line open, further facilitating the free flow of fluid through the medical line.

Figure 6:
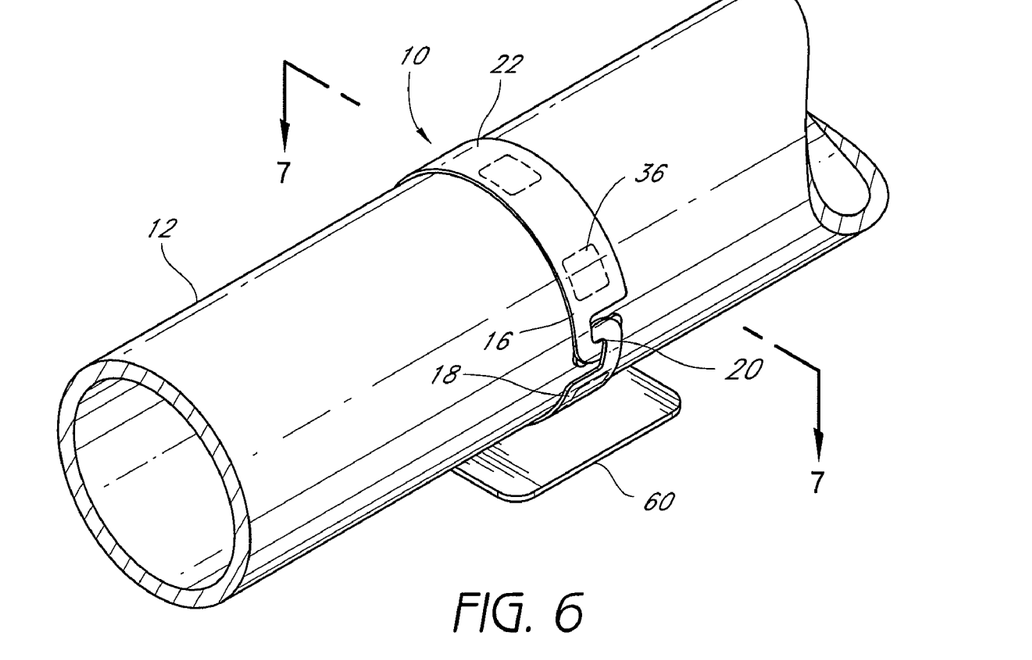
FIG. 6 is a perspective view of the support clamp of FIG. 2 secured around a medical line.
Figure 7:
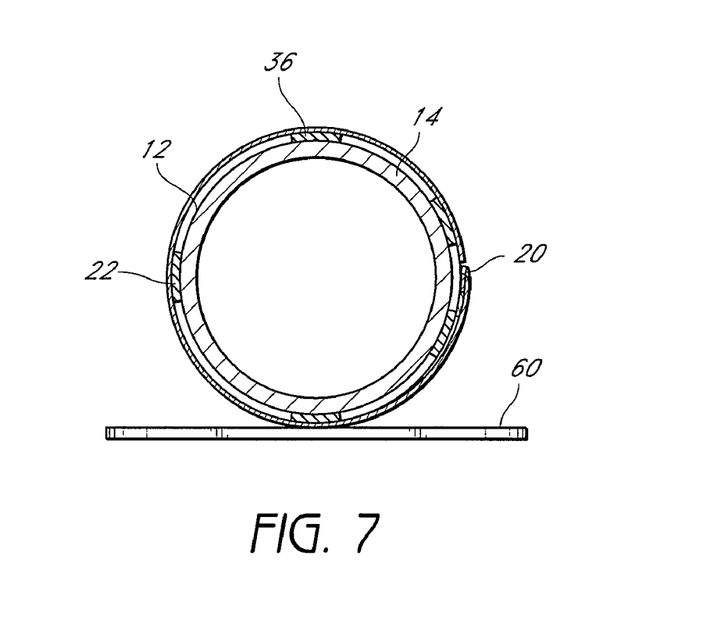
FIG. 7 is a cross-sectional view of the support clamp taken along line 7-7 in FIG. 6.

FIG. 6 is a perspective view of the support clamp 10 of FIG. 2 secured to a medical line 12. In this case, the line 12 is a soft flexible tube that is not rigid, so the tubular walls can be compressed, bent, or creased. FIG. 7 is a cross-section view of the support clamp of FIG. 6 secured to the medical line 12. As can be seen in FIG. 7, the body 14 secures the line 12 to the base 60, which may be affixed directly or indirectly to a patient.

An exemplary method for securing a medical line to a patient using the support clamp of FIG. 6 is now described. The base 60 is released from a release sheet (not shown) and affixed to a patient. The body 14 is in an open configuration or position. The release sheet(s) 38 are removed from the adhesive 36 exposing the adhesive 36. The medical line 12 is placed in the passageway and preferably in contact with at least a portion of the adhesive 36. As the body 14 is closed by interengaging the ends 16 and 18, the adhesive 36 further adheres to the medical line 12 to inhibit movement of the medical line 12 relative to the support clamp 10.

Figure 8A:
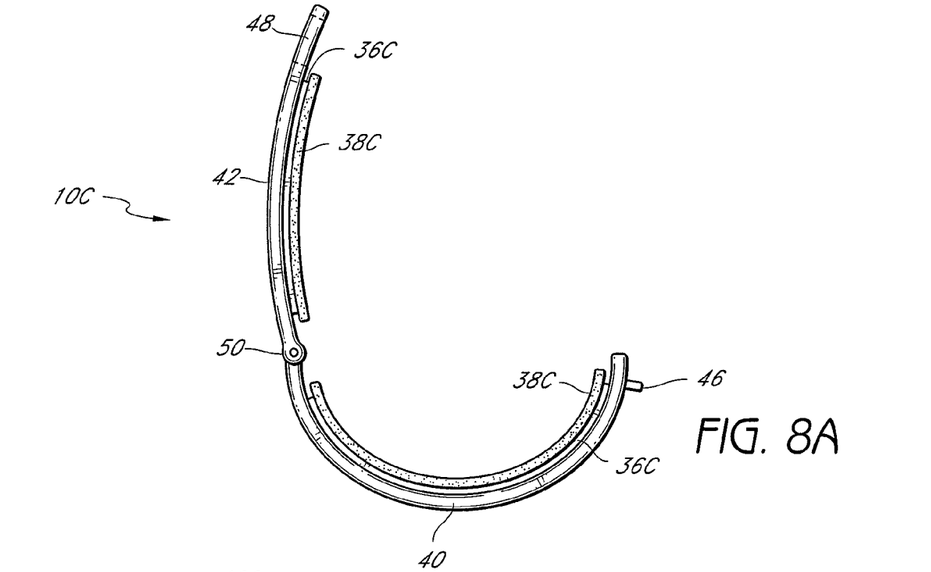
FIG. 8A is a cross-sectional view of another embodiment of a support clamp that has a hinge and is in an open position.
Figure 8B:
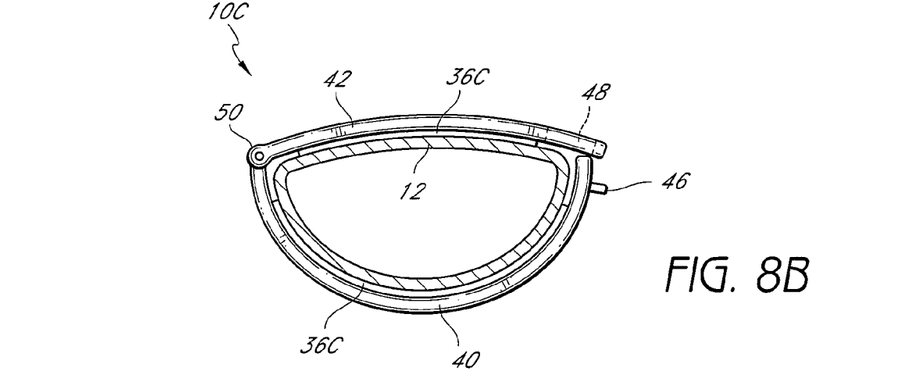
FIG. 8B is a cross-sectional side view of the support clamp of FIG. 8A with a medical line positioned in the clamp before the clamp is moved to a closed position.
Figure 8C:
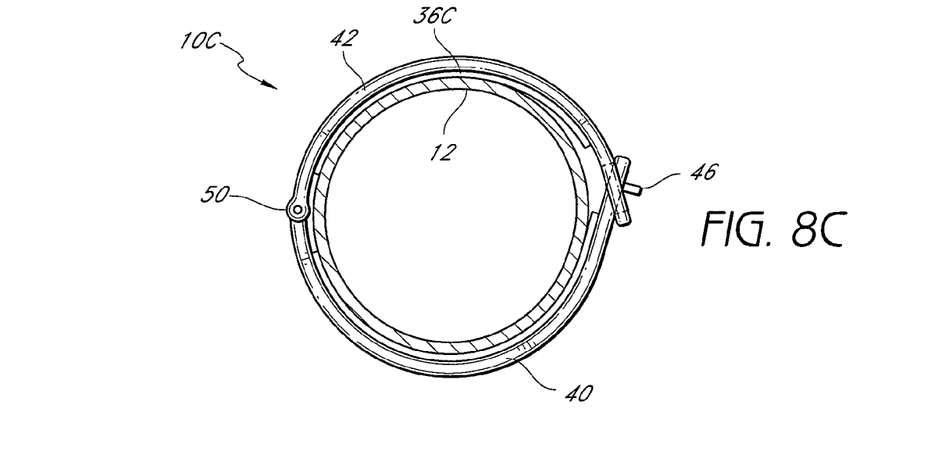
FIG. 8C is a cross-sectional side view of the support clamp of FIG. 8B with the clamp in the closed position.

FIGS. 8A-C are cross-sectional side views of an embodiment of a support clamp 10C that has a hinge 50. FIG. 8A illustrates the support clamp 10C in an open position. FIG. 8B is a cross-sectional side view of the support clamp 10C of FIG. 8A with a medical line 12 positioned in the clamp before the clamp is moved to a closed position. FIG. 8C is a cross-sectional side view of the support clamp of FIG. 8B with the clamp in the closed position.

FIG. 8A shows the clamp 10C in an open position prior to installation with a release sheet 38C in place. To install the clamp 10C on a line 12, the release sheet 38C, if used, is removed from the adhesive 36C to expose the tacky surface. The line 12 is placed within the clamp against a portion of the body, in this case the first piece 40. The second piece 42, or remainder of the body, is then pressed down on the line 12 so that it contacts and adheres to the opposed wall of the line 12, as shown in FIG. 8B. Then the interengaging structure is secured. For example, the interengaging structure can include a projection 46 and slot 48. The projection 46 can be inserted into the slot 48. When engages the first and second pieces 40, 42, at least one of the first and second pieces 40, 42 flexes in an outward direction to form at least a portion of a generally circular or ring-like shape. Of course the shape need not be completely circular, as shown in FIG. 8C. With this complementary shape, the walls of the line 12 can maintain its natural shape even when pressure is applied to the line 12 near to the support clamp. In this way, the support clamp 10C holds the line 12 open and inhibits the line from collapsing, kinking, or bending in the region of the support clamp 10C. In some embodiments, the line 12 may be made of a partially stretchable material such that the diameter of the line 12 is increased by the clamp 10C attempting to create a ring-like passageway. By holding the medical line 12 open, the free flow of fluid is facilitated.

In certain embodiments, the interaction between the inner surface of the passageway and the medical line creates friction that may inhibit longitudinal movement through the passageway. The degree of interference between the medical line and the support clamp, however, cannot be so great as to significantly occlude the medical line. For example, the inner surface of the support clamp may include structure, in addition to an adhesive, disposed thereon to enhance the clamp's ability to inhibit movement of the medical line through the passageway. Structure includes, for example, protrusions, securement barbs, and friction ridges.

For example, one or more friction ridges can be located on the inner surface to inhibit axial movement of the medical line. The ridges can be integrally formed with the clamp and project into the passageway. The ridges can be desirably of smooth solid construction; however, they can be of hollow construction. The ridges can have generally triangular cross-sectional shapes and angle toward one end of the passageway. The ridges, however, can have other cross-sectional shapes which would interfere with axial movement of the medical line through the passageway.

One or more securement barbs can also be used to retain the medical line in the longitudinal direction. Each barb can have a generally conical shape with a blunt tip. The barbs can be arranged within the passageway to cooperate with one another. The barbs can be arranged within the same general lateral plane (i.e., a plane defined by the lateral and transverse axes), and spaced apart from one another. In addition, the barbs can be spaced on generally opposite surfaces of the passageway in a staggered arrangement.

The support clamp can be used on any tubular member and may be used singly or as part of support system to keep of length of tubing open. Any of the various interengaging structures, body configurations, and adhesive arrangements disclosed herein or equivalents thereof may be used in combination with each other and are not intended to be limited to the combinations shown herein for descriptive purposes.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure and the claims that follow.

It is to be understood that not necessarily all objects or advantages disclosed herein may be achieved in accordance with any particular embodiment. Thus, for example, those skilled in the art will recognize that embodiments may be carried out in a manner that achieves or optimizes one advantage or group of advantages as taught herein without necessarily achieving other objects or advantages as may be taught or suggested herein. In addition to the variations described herein, other known equivalents for each feature can be incorporated by one of ordinary skill in this art to construct a device and/or system in accordance with principles of this invention.

While the illustrative embodiments have been described with particularity, it will be understood that various other modifications will be apparent to and can be readily made by those skilled in the art without departing from the spirit and scope of the invention. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but by a fair reading of the claims that follow.

What is claimed is:

1. A support clamp for use with a flexible hollow line, comprising:
    an elongated body having two ends and an inner surface, the body being movable between an open position in which at least a portion of the line can be received by the clamp, a closed position in which the body defines a passageway configured to surround at least a received portion of the line, and a secured position, the body having a non-circular shape when in the closed position and a circular shape when in the secured position;
    an adhesive disposed on at least a portion of the inner surface of the passageway and configured to contact at least a portion of the received line; and
    interengaging structure configured to releasably secure the two ends in the secured position, the interengaging structure biasing at least a portion of the body in a generally outwardly direction to form the circular a shape when the body is in the secured position.

2. The support clamp of claim 1, wherein the body is formed of two pieces, with at least one of the pieces being flexible.

3. The support clamp of claim 1 further comprising a hinge in the body and between the two ends.

4. The support clamp of claim 1, wherein the body is formed of at least two portions, with one portion being longer than the other portion.

5. The support clamp of claim 1, wherein the body is formed of two pieces, with one piece being arcuately shaped and having a first length and the other piece having a second length less than the first length.

6. The support clamp of claim 1, wherein at least a portion of the body has a gently curved shaped.

7. The support clamp of claim 1, wherein the adhesive comprises a layer of adhesive material on the inner surface.

8. The support clamp of claim 1, wherein the adhesive is disposed on the inner surface at least at two locations on opposite sides of the body at least when the body is in the closed position.

9. The support clamp of claim 1 further comprising release tape disposed over the adhesive.

10. The support clamp of claim 1, wherein the interengaging structure comprises a receptacle formed on one of the two ends and a projection having at least one tooth formed on the other one of the two ends, and wherein the projection is received in the receptacle and the at least one tooth engages the receptacle to form an interlock.

11. The support clamp of claim 1, wherein the interengaging structure comprises a projection and a slot.

12. A support clamp for use with a medical line having a passage therethrough, comprising:
    a flexible body having opposed ends;
    adhesive disposed on at least a portion of a surface of the flexible body; and
    interengaging structure disposed on the opposed ends of the flexible body to selectively join the ends of the body and form the flexible body into a generally ring shape with the adhesive facing inwardly to form an adhesive lined conduit, the adhesive being on diametrically opposite sides and in tension when contacting a medical line so as to maintain a passage in the medical line in an open condition.

13. The support clamp of claim 12, wherein the flexible body is formed of two pieces hinged together.

14. The support clamp of claim 12 further comprising a base supporting the body.

15. A support clamp comprising:
    a body having interengaging structure, at least a portion of the body being movable between an unrestrained shape in which the interengaging structure is disengaged, and a restrained shape in which the interengaging structure is engaged; and
    adhesive being on diametrically opposite sides and in tension when contacting the medical line at least when the medical line is secured within the clamp and the body is in the restrained shape so as to resist compression of the medical line.

16. The support clamp of claim 15, wherein the restrained shape is generally ring shaped.

17. The support clamp of claim 15, wherein the body is formed of at least two portions and a hinge.

18. The support clamp of claim 15 further comprising a base supporting the body.

* * * * *

UNITED STATES PATENT AND TRADEMARK OFFICE
CERTIFICATE OF CORRECTION

| | |
|---|---|
| PATENT NO. | : 8,146,210 B2 |
| APPLICATION NO. | : 12/175247 |
| DATED | : April 3, 2012 |
| INVENTOR(S) | : Vasu Nishtala |

Page 1 of 1

It is certified that error appears in the above-identified patent and that said Letters Patent is hereby corrected as shown below:

At column 9, line 40, in Claim 1, after "the circular", delete "a".

Signed and Sealed this
Sixth Day of November, 2012

David J. Kappos
*Director of the United States Patent and Trademark Office*